United States Patent
Pontisso et al.

(10) Patent No.: US 11,628,163 B2
(45) Date of Patent: Apr. 18, 2023

(54) 1-PIPERIDINEPROPIONIC ACID FOR TREATING A FIBROSING DISEASE

(71) Applicant: UNIVERSITÀ DEGLI STUDI DI PADOVA, Padua (IT)

(72) Inventors: Patrizia Pontisso, Padua (IT); Alessandra Biasiolo, Padua (IT); Andrea Cappon, Padua (IT); Andrea Martini, Padua (IT); Santina Quarta, Padua (IT); Mariagrazia Ruvoletto, Padua (IT); Cristian Turato, Padua (IT); Gianmarco Villano, Padua (IT)

(73) Assignee: Università degli Studi di Padova, Padua (IT)

( * ) Notice: Subject to any disclaimer, the term of this patent is extended or adjusted under 35 U.S.C. 154(b) by 0 days.

(21) Appl. No.: 16/491,858

(22) PCT Filed: Mar. 9, 2018

(86) PCT No.: PCT/IB2018/051554
§ 371 (c)(1),
(2) Date: Sep. 6, 2019

(87) PCT Pub. No.: WO2018/163119
PCT Pub. Date: Sep. 13, 2018

(65) Prior Publication Data
US 2021/0137905 A1    May 13, 2021

(30) Foreign Application Priority Data
Mar. 10, 2017   (IT) .................. 102017000026858

(51) Int. Cl.
| *A61K 31/4453* | (2006.01) |
| *A61P 1/16* | (2006.01) |
| *A61P 35/04* | (2006.01) |

(52) U.S. Cl.
CPC ........... *A61K 31/4453* (2013.01); *A61P 1/16* (2018.01); *A61P 35/04* (2018.01)

(58) Field of Classification Search
CPC .................................. A61K 31/4453
USPC ...................................... 514/315
See application file for complete search history.

(56) References Cited

U.S. PATENT DOCUMENTS

| 2008/0004317 A1* | 1/2008 | Gabos ............... A61P 11/06 514/333 |
| 2008/0207569 A1* | 8/2008 | Spada ............... A61P 31/14 514/152 |
| 2016/0230226 A1* | 8/2016 | Abbas ............. G01N 33/6893 |

FOREIGN PATENT DOCUMENTS

| JP | 2009-242345 | 10/2009 | |
| WO | WO-2012157587 A1 * | 11/2012 | ........ A61K 31/4453 |

OTHER PUBLICATIONS

JP2009242345A Google translation, (Year: 2009).*
WO2012157587 Google translation (Year: 2012).*
Turato et al. SERPINB3 (serpin peptidase inhibitor, clade B (ovalbumin), member 3), Altas Genet Cytogenet Oncol. Haematol. 2015, vol. 19, No. 3, pp. 202-209 (Year: 2015).*

(Continued)

*Primary Examiner* — Shengjun Wang
(74) *Attorney, Agent, or Firm* — Sterne, Kessler, Goldstein & Fox, P.L.L.C.

(57) ABSTRACT

The present description relates to 1-piperidinepropionic acid or pharmaceutically acceptable salts thereof, or pharmaceutical compositions comprising it, for use in the treatment of chronic fibrosing diseases.

7 Claims, 4 Drawing Sheets

Specification includes a Sequence Listing.

(56) References Cited

OTHER PUBLICATIONS

International Search Report and Written Opinion of the ISA for PCT/IB2018/051554, dated Jun. 13, 2018, 15 pages.
Lunardi et al., "Overexpression of SERPIN B3 promotes epithelial proliferation and lung fibrosis in mice", Laboratory Investigation, vol. 91, No. 6, Mar. 14, 2011, pp. 945-954.
Hibino et al., "Role of caspase-14 in DNA degradation and its Application to Cosmetic Products", Nippon Koshohin Gakkaishi, vol. 34, No. 2, Jan. 1, 2010, 1 page.

* cited by examiner

1-PIPERIDINEPROPIONIC ACID FOR TREATING A FIBROSING DISEASE

CROSS-REFERENCE TO RELATED APPLICATIONS

This application is a U.S. National Phase of PCT Application No. PCT/IB2018/051554, filed Mar. 9, 2018, which claims priority to Italian Patent Application No. 102017000026858, filed Mar. 10, 2017, each of which is incorporated herein by reference in its entirety.

The present description relates to a novel use of serine protease inhibitors, in particular SERPINB3, pharmaceutical compositions for use in the treatment of chronic fibrosing diseases, methods of treatment of chronic fibrosing diseases with said compositions.

STATE OF THE PRIOR ART

SerpinB3 is a member of the serine protease inhibitor family (Serpins), physiologically expressed in squamous epithelia (Kato et al, Anticancer Res. 1996; 199616(4B): 2149-2153). The use of SerpinB3 inhibitors for the treatment of diseases characterized by abnormal cell proliferation, such as tumors, is known in the literature (JP2009242345). In particular, the document teaches the use of a specific inhibitor, 1-piperidinepropionic acid, or of a salt thereof, for the treatment of skin tumors. The technical effect observed on the skin, following topical use of 1-piperidinepropionic acid, as described by the patentees of the aforementioned patent, is a suppression of SerpinB3 with an entailed improvement of barrier functions, hydration-retaining ability, and of skin elasticity and softness, in all respects resulting in an improvement of skin quality.

Various pathological effects linked to SerpinB3 molecule expression are described in the literature, like the induction of activation of various factors, such as pro-oncogenic molecules (e.g., Myc, β-catenin and TGFβ) anti-apoptotic effects, cell proliferation increase, activation of inflammatory cytokines (e.g., IL-6 and TNF-α), inhibition of intratumor infiltration of natural killer cells, etc.

Fibrosing diseases are chronic pathologies, with a different genesis, characterized by various types of cellular or extracellular infiltrates determining a progressive destruction of the parenchyma, which is replaced by fibrous tissue, causing a progressive damage to organ anatomy.

To date, no effective drugs are available for the treatment of fibrosing diseases. A series of possible therapeutic targets have been identified, yet to this day active ingredients actually effective in the treatment of said pathologies have not been singled out.

Since fibrosing diseases are one of the main causes of morbidity and mortality in the Western world, it is evident how the singling out of active ingredients effective in the treatment of such diseases be of marked interest in the medical field.

SUMMARY OF THE INVENTION

The Authors of the present invention have identified, as effective target for the treatment of fibrosing diseases, the molecule SerpinB3.

In fact, the Authors have demonstrated, in murine models, that the administration of 1-piperidinepropionic acid is able to inhibit the progression of fibrosing diseases.

Therefore, object of the invention is 1-piperidinepropionic acid or a salt thereof, or compositions comprising it for use in the treatment of fibrosing diseases. Object of the invention are also therapeutic methods for the treatment of fibrosing diseases, wherein the composition or the formulation according to the invention is administered to a subject in need thereof.

GLOSSARY

Fibrosing diseases. The term fibrosing diseases in the present description has the meaning commonly used by the technician in the field. According to scientific literature, fibrosing diseases are chronic pathologies with a different genesis, characterized by various types of cellular or extracellular infiltrates determining a progressive destruction of the parenchyma, which is replaced by fibrous tissue, causing a progressive damage to the anatomical structure of the organ. Various examples of fibrosing diseases are provided in the detailed description of the invention.

1-piperidinepropionic acid (herein also referred to as PPA) (CAS Registry Number: 26371-07-3) also denominated 1-Piperidine-propanoic acid or 3-(1-Piperidinyl)propionic acid, or piperidinepropionic acid, is an amino acid of formula SerpinB3: known as Squamous Cell Carcinoma Antigen, SCCA1, belonging to ov-serpins, it is normally expressed in squamous epithelia, but is found hyper-expressed in neoplastic cells of epithelial origin and in hepatocarcinoma. Serpins are a family of serine protease inhibitors involved in many biological functions and in cell homeostasis control processes. SerpinB3 can affect cell mobility, invasivity, proliferation and death itself.

DETAILED DESCRIPTION OF THE INVENTION

Therefore, the present invention provides for the first time an agent effective in the treatment of fibrosing diseases. The Authors of the invention have in fact discovered and demonstrated that 1-piperidinepropionic acid is effective in the treatment of fibrosing diseases. Data obtained on transgenic mice show in fact how the treatment with this substance, following treatments with compounds inducing the onset of fibrosing pathologies, leads to a visible reduction of tissue damage and fibrotic state of the tissue analyzed. In Example 3 below, there are reported in detail the experimental data demonstrating the effectiveness of 1-piperidinepropionic acid as active ingredient with therapeutic effect for the treatment of fibrosing diseases. By chronic fibrosing diseases, chronic and non-chronic ones, are meant all those diseases commonly defined as such by the technician in the field. A non-limiting example of such diseases includes fatty liver, steatohepatitis, hepatic cirrhosis, idiopathic pulmonary fibrosis, connective tissue disease, Immunoglobulin IgG4 sclerosing diseases, sclerosing cholangitis, nephrogenic systemic fibrosis, kidney fibrosis, muscular fibrosis, scleroderma, scleredema, graft versus host disease, eosinophilic fasciitis, scleromyxedema. In one embodiment of the invention, 1-piperidinpropionic acid may be replaced by or in combination with a pharmaceutically acceptable salt thereof. By "connective tissue disease" are meant those systemic autoimmune rheumatic diseases commonly denominated "connective tissue disease", which are characterized by a frequent involvement of the musculoskeletal apparatus, with autoimmune pathogenesis and a broad tissue involvement. In particular, in scleroderma a process of inflammation/fibrosis of lung parenchyma, hollow viscera (specifically, esophagus) and derma is frequently found, leading to progressive stiffening and organ damage.

By "Immunoglobulin IgG4 sclerosing diseases" are meant those pathological sclerosing forms characterized by high serum levels of Immunoglobulins G4, having swelling (volume increase) of organs involved, a variable degree of fibrosis and an infiltrate enriched in IgG4-positive plasma cells. The main form is autoimmune pancreatitis, but the disease can affect any organ, such as, e.g., salivary glands, orbits, retroperitoneum.

Primitive sclerosing cholangitis is a biliary system disease causing chronic inflammation and progressive fibrosis of biliary ducts. Over time, this process causes progressive damage to the liver, down to cirrhosis.

Nephrogenic systemic fibrosis, or nephrogenic fibrosing dermopathy, is a rare and serious syndrome causing fibrosis of skin, joints, eyes and internal organs. Patients develop wide areas of hardened skin, with fibrotic nodules. It can also cause joint contractures, with entailed pain and limitation of motion. In its gravest form it can cause a serious systemic fibrosis affecting internal organs, among which lungs, heart and liver.

(Chronic) kidney fibrosis exhibits a progression and accumulation of fibrosis in the renal parenchyma that is markedly variable from patient to patient, even in the presence of the same underlying nephropathies and comorbidities, yet its mechanisms are still not known.

In chronic muscle diseases, tissue self-repair generates fibrosis. If tissue damage persists and becomes chronic, as in case of muscular dystrophies, or in the ageing process, the repair becomes uncontrolled and can lead to replacement of muscle fibers with a non-functional fibrotic mass, and development of muscular fibrosis. Vascular stem cells, following a damage, can change their destiny and generate matrix-depositing cells (by endothelial to mesenchymal, or EndoMT transition).

In one embodiment of the invention, 1-piperidinepropionic acid is used to reduce hepatic damage, by reducing the inflammatory component and the activation of the cell component accountable for fibrosis in patients suffering from steatohepatitis.

According to a further aspect of the present invention, 1-piperidinepropionic acid can be used for the treatment of chronic sclerosing diseases, such as hepatic cirrhosis and idiopathic pulmonary fibrosis. Without being bound to theory, it is believed that the active ingredient acts by slowing down the inflammatory process, and of progressive fibrosis underlying such pathologies.

The Authors of the invention have observed that 1-piperidinepropionic acid is able to reduce chronic damage and the development of fibrosis in the liver, as it significantly reduces inflammation and the activation of hepatic stellate cells, which are the main effectors of the fibrogenetic process. The Authors of the invention have in fact observed, as reported in Example 4, that 1-piperidinepropionic acid significantly reduces the levels of alpha-SMA, which is the reference marker for stellate cell activation.

According to a further embodiment of the present invention, 1-piperidinepropionic acid is used to significantly reduce the synthesis of chemokine MCP1 (monocyte chemoattractant protein 1) which is one of the main factors accountable for the recruitment of monocytes concurring to the inflammation and fibrogenesis process.

The Authors of the invention also demonstrated that 1-piperidinepropionic acid is able to block the release of cytokine soluble receptor CD163 (sCD163) induced by SerpinB3 in primary human monocytes.

PPA dosage could be established by the physician on the basis of the weight, health state, gender and age of the patient to be treated.

In one embodiment, said active ingredient could be administered in a unit dose of between 0.01 mg and 10 mg y, preferably between 0.05 mg and 5 mg, even more preferably between 0.1 mg and 1 mg.

Object of the invention is also a pharmaceutical composition for the treatment of fibrosing diseases as defined above, comprising 1-piperidinepropionic acid or a salt thereof and at least one pharmaceutically acceptable carrier.

By way of example, the composition according to the present description could comprise from 0.01 mg to 10 mg y, preferably from 0.05 mg to 5 mg, even more preferably from 0.1 mg to 1 mg of PPA as unit dose, and one or more doses (or fractions of doses) of said composition could be administered to the patient. Alternatively, the composition could be suitably metered according to the opinion of the doctor in charge.

The composition according to the invention could be a composition for parenteral, oral, nasal, aerosol, systemic administration, and could be formulated in the form of suspension, emulsion, cream, spray, granules, powder, solution, capsule, tablet, pill, lyophilized product, lozenge, intramuscular or intravenous injection according to conventional pharmaceutical formulation techniques, with suitable excipients, carriers, preservatives, diluents and the like. Such further components for the formulation of the pharmaceutical composition could be selected from technological excipients or adjuvants used in common pharmaceutical, cosmetics practice, or in food industry. The excipients used could belong to the categories of diluents, solubilizers, disgregants, binders, lubricants, surfactants, sliding and anti-adhering agents.

In one embodiment, the composition can also contain flavorings, coloring agents and preservatives of common use in the pharmaceutical industry.

In accordance with the invention, experiments were conducted on PPA activity on murine models of fibrosing pathologies.

The experiments conducted by the Authors of the invention demonstrated that very low PPA concentrations (100 ng/ml) are able to inhibit SerpinB3 synthesis in certain cell lines (e.g., HT-29 line) constitutively expressing this serpin.

PPA effect was also assessed in a murine model of fibrosing disease, in particular an experimental model of non-alcoholic steatohepatitis, which is a condition in which a fatty liver, associated with inflammation and fibrosis production, causes, among other things, a high risk of neoplastic transformation. In the study, both SerpinB3-transgenic mice and the respective wild-type (C57BL/7) strain were used, fed for 8 weeks with a methionine- and choline-deficient diet (MCD), which constitutes a recognized steatohepatitis induction model, or with a normal diet. MCD diet-treated transgenic and control mice groups starting from Week 4, were administered daily by intraperitoneal route, PPA (0.01 µg/g), or Curcumin (a molecule with a recognized anti-inflammatory and anti-fibrotic activity in animal models) as control, at standard concentrations (0.2 mg/g).

Upon being sacrificed, the livers of MCD diet-fed mice exhibited a more marked steatosis, associated with a higher relative liver weight, compared to mice MCD diet-fed, but treated with PPA or curcumin, especially SerpinB3-transgenic ones (this experiment is described in detail in Example 3 below).

In both PPA-treated strains, a marked reduction of alpha-SMA, a marker of activation of stellate cells, which are the main components involved in hepatic fibrogenesis, was recorded. Moreover, in SerpinB3-transgenic mice a significant decrease of inflammatory cytokine IL-1beta and of Mcp1 molecule, involved in macrophage recruitment, was also recorded during inflammation, whereas TNF-alpha increase was non-evident, unlike what observed in wild-type mice subjected to MCD and treated with PPA (Example 3). It is important to point out that the effects observed on the reduction of the inflammatory response were obtained also with curcumin, used as control, but with effective PPA doses 20.000 times lower.

The anti-inflammatory effect of PPA was also confirmed on primary human monocyte lines, in which, in preliminary results, the Authors had documented that SerpinB3 addition (200 ng/ml) induces the release of cytokine soluble receptor CD163 (sCD163), a recently described molecule, increased in a wide range of inflammatory diseases and produced by monocytes. The results obtained documented that sDC163 release in the culture medium alter one week of stimulation with SerpinB3 is markedly reduced in the presence of PPA at 100 ng/ml (this experiment is described in detail in Example 3 below).

EXPERIMENTAL RESULTS

EXAMPLE 1

PPA Inhibits SerpinB3 Synthesis

HT29 tumor cells, constitutively expressing SerpinB3, were used, $65 \times 10^5$ cells/well were seeded into 6-well plates and kept 24 hours prior to treatment in modified McCoy medium (Sigma-Aldrich, Milan, Italy) supplemented with heat-inactivated 10% fetal calf serum, (Sigma-Aldrich, Milan, Italy), 100 U/ mL penicillin, 100 mg/ml streptomycin, and 20 mM L-glutamine (Sigma-Aldrich, Milan, Italy), Then, PPA (1'-piperidinepropionic acid) was added, at a concentration of 100 ng/ml alone or in combination with recombinant SerpinB3 (SB3) at a concentration of 200 ng/ml, whereas the medium alone (untreated HT-29 cells) was added into control wells. After 24 hours of treatment cells were harvested, and extraction of total cell RNA and reverse transcription were performed according to standard protocols. mRNA SerpinB3 levels were measured by real-time PCR (sense: 5'-GCA AAT GCT CCA GAA GAA AG-3'; reverse 5'-CGA GGC AAA ATGAAAA AGA TG-3') and the results were normalized on the basis of data obtained with housekeeping HPRT1 (sense 5'-TCAGGCAGTATAATCC AAAGATGGT-3'; reverse 5'-CTTCGTGGGGTCCTTTTCAC -3').

Figure 1:
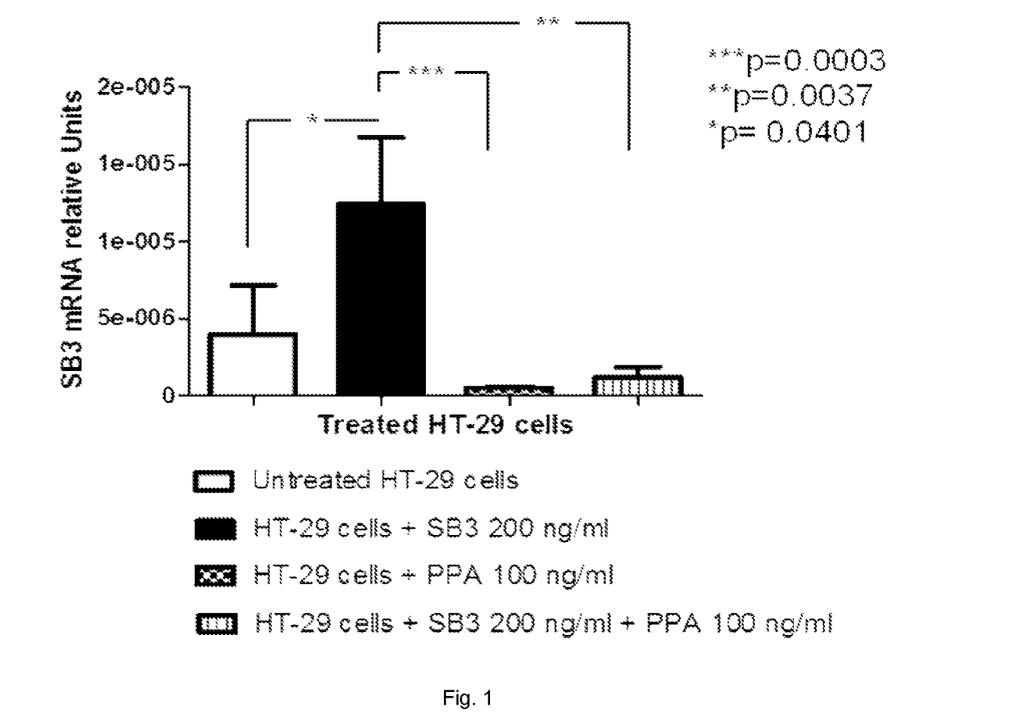
FIG. 1 shows the pattern of SerpinB3 expression following treatment with exogenous SerpinB3, and following PPA addition; PPA proved able to significantly reduce serpinB3 expression, both constitutive and after induction from exogenous treatment.
Figure 2:
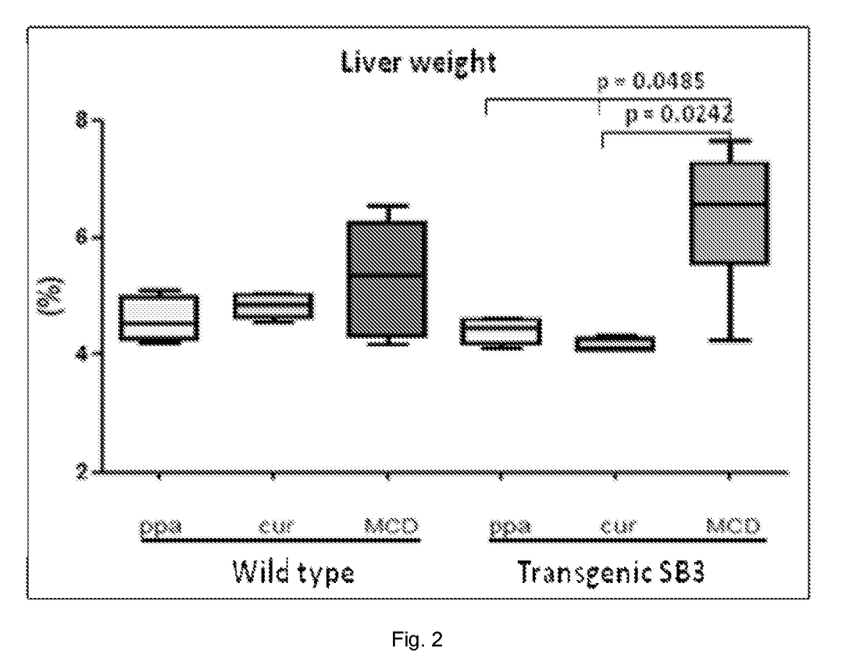
FIG. 2 shows some histograms related to mice liver weight increase due to morphological modifications at the histological level, characterized by a relevant steatosis and presence of lobular damage; the weight is reduced after treatment both with PPA and Curcumin, used as reference compound.

From an assessment of FIG. 1, it clearly emerges that SerpinB3 expression proved to be increased by the treatment with exogenous SerpinB3, and PPA addition proved able to significantly reduce its expression, both constitutive and after induction from the exogenous treatment.

EXAMPLE 2

PPA Reduces Inflammatory Damage in an Animal Model of Steatohepatitis

To assess PPA effect as SerpinB3 inhibitor in an experimental murine model of steatohepatitis (NASH), a condition with a high risk of hepatic tumor, both SerpinB3-transgenic mice and the respective wild-type (C57BL/7) strain were used.

The animals were fed for 8 weeks with a methionine- and choline-deficient diet (MCD), a recognized steatohepatitis induction model, or with a normal diet. MCD diet-treated transgenic and control mice groups, starting from Week 4, were administered daily, by intraperitoneal route, PPA (0.01 µg/g), or Curcumin (a molecule with a recognized anti-inflammatory and anti-fibrotic activity in animal models) as control, at the standard concentration of 0.2 mg/g. Upon being sacrificed, both wild-type and SerpinB3 transgenic mice exhibited a higher relative liver weight (liver weight/body weight) after MCD diet, compared to mice treated with the same diet, in which, starting from Week 4, PPA (ppa) or Curcumin (cur) had been administered. This effect was more evident in transgenic mice.

Figure 3:
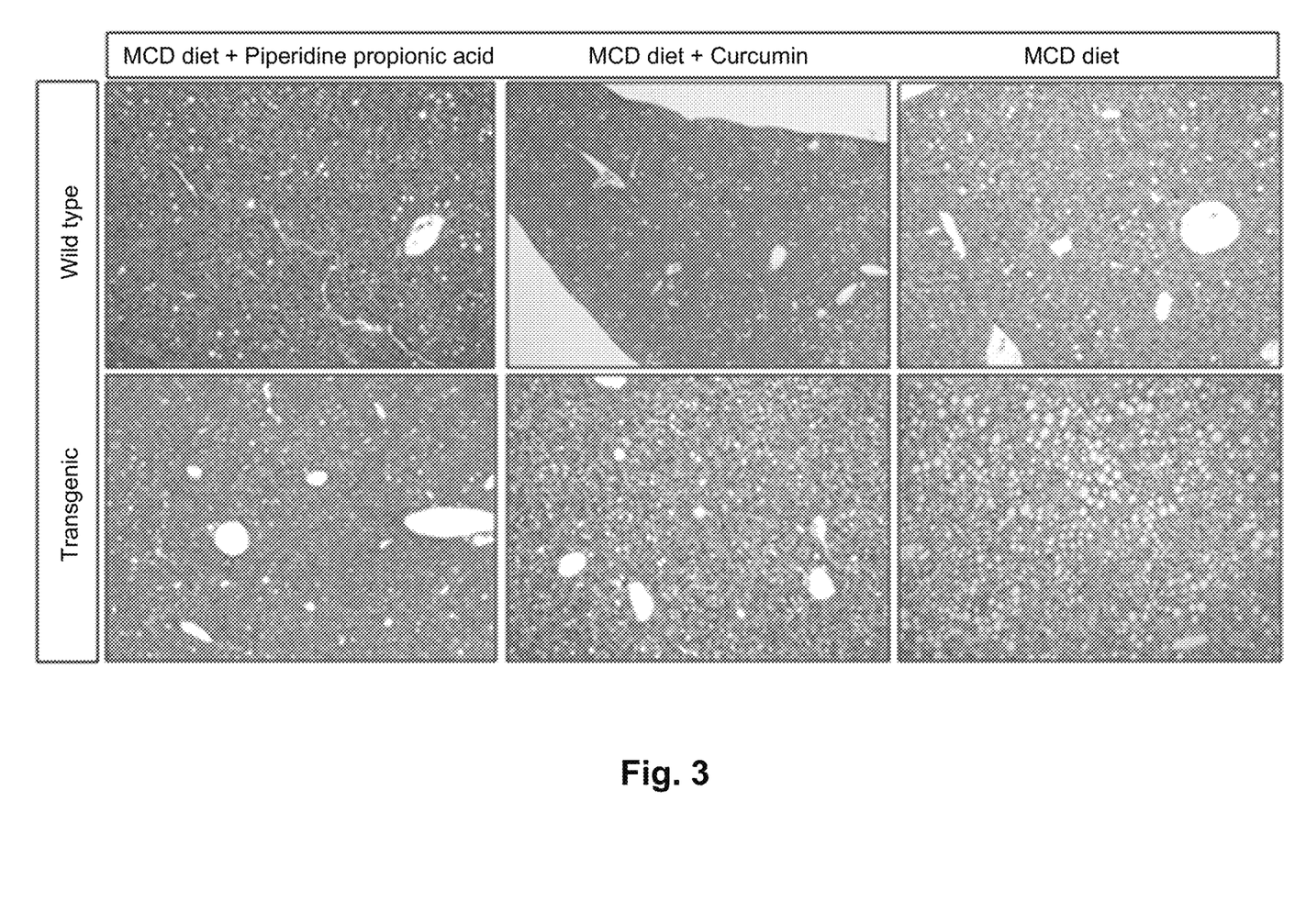
FIG. 3 shows histological sections of liver of mice treated with methionine and choline as described in Example 2. The figure shows that there are evident morphological modifications at the histological level, characterized by a relevant steatosis and presence of lobular damage, in the liver of transgenic mice treated with methionine and choline, and that these modifications are instead reduced after treatment both with PPA and with Curcumin.

As can be seen from FIG. 3, to these macroscopic findings there were associated morphological modifications at the histological level, characterized by relevant steatosis and presence of lobular damage, especially in transgenic mice liver, which proved reduced after treatment both with PPA and with Curcumin.

Figure 4:
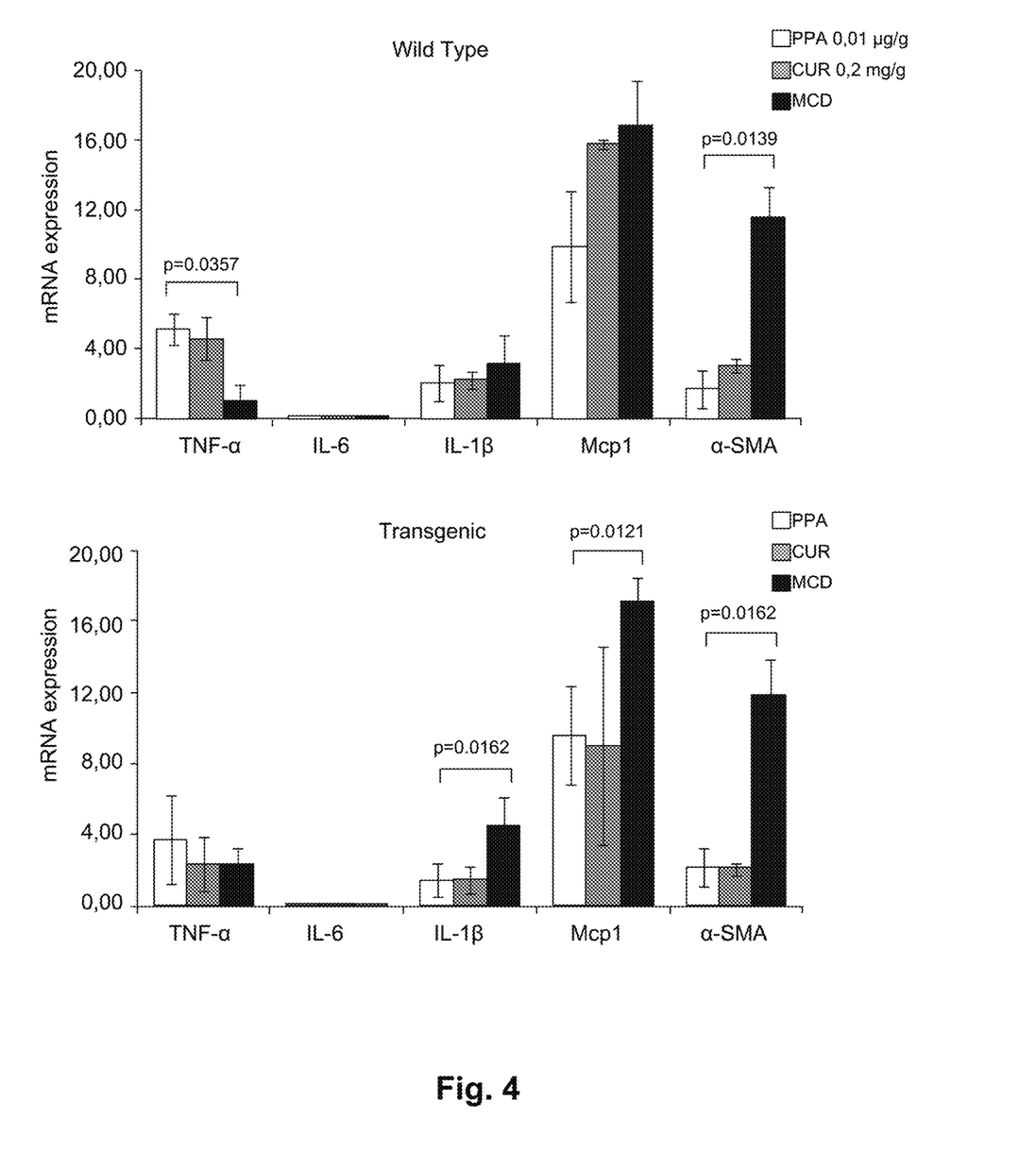
FIG. 4 shows the pattern of mRNA expression of wild mice treated with PPA, curcumin, compared to a control strain.

As to the profile of genes involved in inflammation and fibrosis, in both of the PPA-treated strains a marked reduction of alpha-SMA, a marker of stellate cell activation, was recorded. Moreover, in SerpinB3 transgenic mice, also a significant decrease of IL-1 beta and molecule Mcp1, involved in macrophage recruitment to inflammation, was recorded, whereas TNF-alpha increase proved not evident, unlike what observed in wild-type mice subjected to MCD and treated with PPA (FIG. 4).

EXAMPLE 3

PPA Inhibits SerpinB3-Induced sDC163 in Primary Human Monocytes

Preliminary results obtained in the Authors' laboratory documented that in primary human monocytes SerpinB3 induces the release of cytokine soluble receptor CD163 (sCD163), a recently described molecule, increased in a wide range of inflammatory diseases and produced by monocytes.

PPA effect was evaluated in this context as well, where primary monocytes incubated 1 week with SerpinB3 at a concentration of 200 ng/ml alone, or in association with PPA (100 ng/ml) were used. Monocytes kept in culture medium and monocytes treated with PPA alone at the same concentrations were used as controls.

Figure 5:
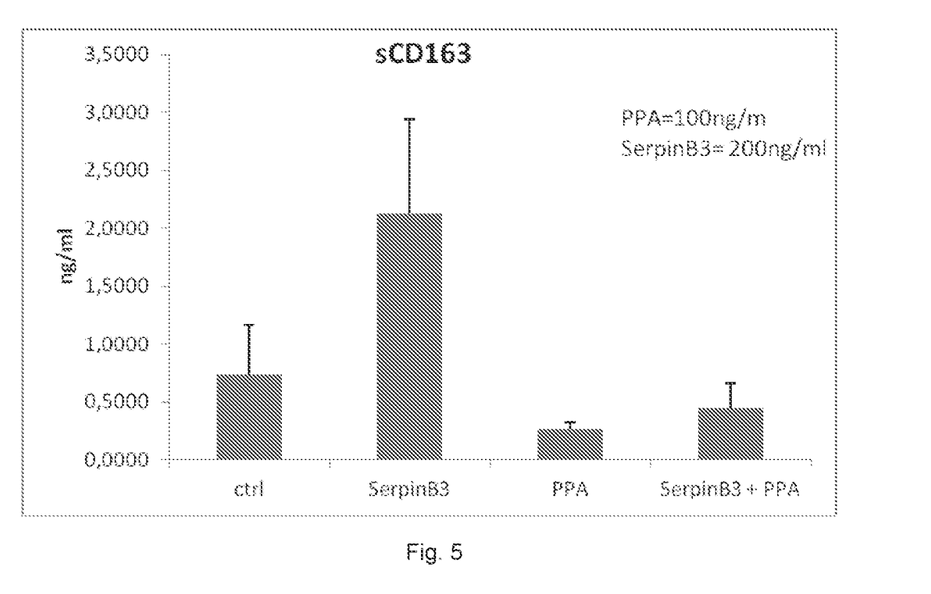
FIG. 5 shows the pattern of mRNA expression of transgenic mice treated with PPA, curcumin, compared to a control strain.

The results obtained documented that sDC163 release in the culture medium after 1 week of stimulation with SerpinB3 is markedly reduced in the presence of PPA. Moreover, this molecule also reduces the spontaneous release of sCD163, observed in untreated monocytes (FIG. 5).

The invention claimed is:

1. A method for treating non-alcoholic steatohepatitis in a subject in need thereof, comprising administering to the subject a pharmaceutical composition comprising 1-piperidinepropionic acid or a salt thereof at a concentration of between 0.01 mg and 10 mg per unit dose and at least one pharmaceutically acceptable carrier, wherein said administering is parenteral, oral, nasal, aerosol, sublingual or systemic administration.

2. The method of claim 1, wherein said administering reduces the level of alpha-SMA.

3. The method of claim 1, wherein said administering reduces the level of MCP1.

4. The method of claim 1, wherein said pharmaceutical composition comprises 1-piperidinepropionic acid or a salt thereof at a concentration of between 0.05 and 0.5 mg per unit dose.

5. The method of claim 1, wherein said pharmaceutical composition comprises 1-piperidinepropionic acid or a salt thereof at a concentration of between 0.01 and 0.1 mg per unit dose.

6. The method of claim 1, wherein said pharmaceutical composition further comprises one or more ingredients selected from stabilizers, diluents and pharmaceutically acceptable excipients.

7. The method of claim 1, wherein said pharmaceutical composition is in the form of suspension, spray, granules, powder, solution, capsule, tablet, pill, lyophilized product, lozenge or injection.

* * * * *

SEQUENCE LISTING

<160> NUMBER OF SEQ ID NOS: 1

<210> SEQ ID NO 1
<211> LENGTH: 1398
<212> TYPE: DNA
<213> ORGANISM: Lysinibacillus fusiformis

<400> SEQUENCE: 1

```
cagtcgagcg aacagagaag gagcttgctc cttcgacgtt agcggcggac gggtgagtaa      60
cacgtgggca acctacctta tagtttggga taactccggg aaaccggggc taataccgaa     120
taatctgttt cacctcatgg tgaaacactg aaagacggtt tcggctgtcg ctataggatg     180
ggcccgcggc gcattagcta gttggtgagg taacggctca ccaaggcgac gatgcgtagc     240
cgacctgaga gggtgatcgg ccacactggg actgagacac ggcccagact cctacgggag     300
gcagcagtag ggaatcttcc acaatgggcg aaagcctgat ggagcaacgc cgcgtgagtg     360
aagaaggatt tcggttcgta aaactctgtt gtaagggaag aacaagtaca gtagtaactg     420
gctgtacctt gacggtacct tattagaaag ccacggctaa ctacgtgcca gcagccgcgg     480
taatacgtag gtggcaagcg ttgtccggaa ttattgggcg taaagcgcgc gcaggtggtt     540
tcttaagtct gatgtgaaag cccacggctc aaccgtggag ggtcattgga aactgggaga     600
cttgagtgca gaagaggata gtggaattcc aagtgtagcg gtgaaatgcg tagagatttg     660
gaggaacacc agtggcgaag gcgactatct ggtctgtaac tgacactgag gcgcgaaagc     720
gtggggagca aacaggatta gataccctgg tagtccacgc cgtaaacgat gagtgctaag     780
tgttaggggg tttccgcccc ttagtgctgc agctaacgca ttaagcactc cgcctgggga     840
gtacggtcgc aagactgaaa ctcaaaggaa ttgacggggg cccgcacaag cggtggagca     900
tgtggtttaa ttcgaagcaa cgcgaagaac cttaccaggt cttgacatcc cgttgaccac     960
tgtagagata tagtttcccc ttcgggggca acggtgacag gtggtgcatg gttgtcgtca    1020
gctcgtgtcg tgagatgttg ggttaagtcc cgcaacgagc gcaacccttg atcttagttg    1080
ccatcattta gttgggcact ctaaggtgac tgccggtgac aaaccggagg aaggtgggga    1140
tgacgtcaaa tcatcatgcc ccttatgacc tgggctacac acgtgctaca atggacgata    1200
caaacggttg ccaactcgcg agagggagct aatccgataa agtcgttctc agttcggatt    1260
gtaggctgca actcgcctac atgaagccgg aatcgctagt aatcgcggat cagcatgccg    1320
cggtgaatac gttcccgggc cttgtacaca ccgcccgtca caccacgaga gtttgtaaca    1380
cccgaagtcg gtgaggta                                                  1398
```